(12) United States Patent
Franklin

(10) Patent No.: US 7,504,091 B2
(45) Date of Patent: Mar. 17, 2009

(54) ANTIPERSPIRANT COMPOSITIONS

(75) Inventor: Kevin Ronald Franklin, Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 484 days.

(21) Appl. No.: 11/105,131

(22) Filed: Apr. 13, 2005

(65) Prior Publication Data

US 2005/0232881 A1    Oct. 20, 2005

(30) Foreign Application Priority Data

Apr. 14, 2004    (GB) .................................. 0408288.9

(51) Int. Cl.
| | |
|---|---|
| A61K 8/00 | (2006.01) |
| A61K 8/02 | (2006.01) |
| A01N 25/08 | (2006.01) |
| A01N 59/26 | (2006.01) |
| A01N 31/14 | (2006.01) |
| A01N 37/00 | (2006.01) |
| A01N 37/10 | (2006.01) |

(52) U.S. Cl. .................... 424/65; 424/401; 424/409; 424/601; 514/715; 514/721; 514/506; 514/543; 514/544

(58) Field of Classification Search .................. 424/65, 424/401, 409, 601; 514/715, 721, 506, 543, 514/544

See application file for complete search history.

(56) References Cited

U.S. PATENT DOCUMENTS

| | | | |
|---|---|---|---|
| 3,557,167 A | 1/1971 | Hülsmann et al. ........ 260/410.5 |
| 6,248,312 B1 | 6/2001 | Franklin et al. ................ 424/65 |
| 6,361,766 B1 | 3/2002 | Franklin et al. ................ 424/65 |
| 6,387,358 B2 | 5/2002 | Chuah et al. .................. 424/65 |
| 6,410,001 B1 | 6/2002 | Franklin et al. ................ 424/65 |
| 6,410,003 B1 | 6/2002 | Bhatia et al. .................. 424/65 |
| 6,610,279 B2 | 8/2003 | Chopra et al. .................. 424/65 |
| 6,635,775 B1 | 10/2003 | Walele et al. ................ 554/175 |
| 6,645,475 B2 | 11/2003 | Franklin et al. ................ 424/65 |
| 6,652,843 B2 | 11/2003 | Fairclough et al. ............ 424/65 |
| 2002/0051757 A1* | 5/2002 | Clare et al. .................... 424/65 |
| 2002/0055562 A1 | 5/2002 | Butuc ........................... 524/80 |
| 2003/0086884 A1* | 5/2003 | Franklin et al. ................ 424/65 |
| 2004/0022750 A1* | 2/2004 | Lee et al. ...................... 424/66 |
| 2005/0226829 A1* | 10/2005 | Burgo ........................... 424/63 |

FOREIGN PATENT DOCUMENTS

| | | |
|---|---|---|
| EP | 455 373 | 12/1994 |
| EP | 1 374 843 | 1/2004 |

OTHER PUBLICATIONS

Merriam-Webster Online Dictionary, 2005, http://w.meriam-webster.com.*
Knovel Critical Tables. (2003). (p. 1). Knovel. Online version available at:http://www.knovel.com/knovel2/Toc.jsp?BookID=761&VerticalID=0.*
Funahashi, Bulletin of the Chemical Society of Japan, 1979, 1488-1492.*

* cited by examiner

*Primary Examiner*—Johann R Richter
*Assistant Examiner*—Abigail Fisher
(74) *Attorney, Agent, or Firm*—Karen E. Klumas

(57) ABSTRACT antiperspirant compositions comprise an antiperspirant active and a carrier oil in which the carrier oil comprises an aromatic ester oil obeying the general formula:

$$R^1-CO_2-X-Y-R^2$$

in which $R^1$ and $R^2$ each represent a phenyl group, X represents an alkylene group containing from 2 to 4 carbons including at least one pendant alkyl group and Y represents a bond, or an ether or ester linkage.

13 Claims, No Drawings

ANTIPERSPIRANT COMPOSITIONS

The present invention relates to antiperspirant compositions and in particular to compositions in which a carrier for an antiperspirant active comprises an ester oil and to a non-therapeutic method for ameliorating body odour or inhibiting perspiration.

TECHNICAL FIELD

Background and Prior Art

Conventionally antiperspirant compositions can be divided into three classes; particulate mixtures of an antiperspirant active and other constituents, solutions of the antiperspirant active in compatible liquid such as water or water-miscible alcohols and thirdly those in which the antiperspirant active is suspended as a solid or a solution in a carrier liquid commonly comprising at least one water-immiscible oil. Herein, oil indicates that the water-immiscible compound is liquid at 25° C. In this third class of compositions, the carrier oil or mixture of oils significantly affects the perception of the product by the consumer, including the appearance and feel of the product. Many different classes of oils have been employed or proposed as carrier oils for antiperspirant actives, sometimes as primary carrier and sometimes in a smaller proportion as an emollient oil. Such a list includes aliphatic alcohols, aliphatic esters, alkyl benzoate esters, naphthalate esters, glyceryl esters, alkyl ethers, hydrocarbon oils and linear and cyclic alkyl or alkyl/aryl substituted siloxanes. Not only does the oil blend affect the properties of the eventual antiperspirant product, but it can also affect the ease of preparation of the product, a factor that can be of commercial significance.

In a number of respects various aromatic esters exhibit desirable properties for use as carrier for antiperspirant actives, or at least as a significant component of a carrier oil blend. Thus, an often quoted constituent of a carrier oil blend is an alkyl benzoate, for example as described in U.S. Pat. No. 6,361,766 and U.S. Pat. No. 6,645,475. Many antiperspirant stick or soft solid compositions in which a carrier oil (blend) is gelled by chosen gellant contemplate ester oils as a fraction of the blend, for example in U.S. Pat. No. 6,361,766, U.S. Pat. No. 6,645,475, U.S. Pat. No. 6,248,312, U.S. Pat. No. 6,410,001, U.S. Pat. No. 6,387,358, U.S. Pat. No. 6,410,003, and U.S. Pat. No. 6,652,843. The benzoate esters described in such patent specifications assist in refractive index matching of the antiperspirant active with the carrier oil, but in general they have only an intermediate refractive index. Unfortunately their RI is too low to contemplate use as the principle carrier oil where RI matching with an activated aluminium chlorohydrate or an aluminium-zirconium antiperspirant active is concerned and constrains the choice of alternative carrier oils that a formulator can employ, even for aluminium chlorohydrate. Accordingly, the formulator faces an unfulfilled want, namely having available an ester oil having a significantly higher refractive index than that of currently available alkyl benzoates, such as $C_{12-15}$ alkyl benzoates.

A few alternatives to alkyl benzoate ester oils are known. Thus, U.S. Pat. No. 6,610,279 discloses the use of naphthalate ester oils. Likewise other patent specifications disclose the use of benzyl benzoate as a component of the carrier liquids. Whilst such compounds tend to have relatively high refractive indexes, their use can be constrained by them imparting inferior sensory properties to antiperspirant formulations containing them. Accordingly, the formulator of antiperspirant compositions is still seeking an alternative ester oil which combines the advantageous properties of a refractive index that is higher than that of $C_{12-15}$ alkyl benzoates with sensory properties that are superior to benzyl benzoate.

SUMMARY OF THE INVENTION

According to the present invention there is provided an antiperspirant composition according to claim 1 hereinafter.

The selection of the esters in accordance with general formula 1, viz $R^1$—$CO_2$—X—Y—$R^2$ enables the formulator of antiperspirant compositions to satisfy his desire simultaneously to employ an ester oil having a refractive index that is higher than that of $C_{12-15}$ alkyl benzoates with sensory properties that are superior to benzyl benzoate.

In a further aspect, there is provided a cosmetic, i.e. non-therapeutic, method for reducing body odour or inhibiting perspiration by the topical application to skin of an antiperspirant composition satisfying claim 1.

DETAILED DESCRIPTION AND PREFERRED EMBODIMENTS OF THE INVENTION

It is an essential feature of this invention that the antiperspirant compositions comprise a carrier oil comprising an ester oil having a refractive index greater than that of $C_{12-15}$ alkyl benzoates, as does benzyl benzoate, but simultaneously avoiding to at least some extent the sensory negative of benzyl benzoate. This is achieved by interposing an alkylene moiety, and optionally an ester or ether linkage between terminal aryl moieties.

In the invention general formula 1, $R^1$—$CO_2$—X—Y—$R^2$ $R^1$ and $R^2$ are both phenyl groups, preferably phenyl itself ($C_6H_5$—) although it may be substituted by a compatible substituent such as alkyl (e.g. methyl). $R^1$ and $R^2$ are preferably the same.

X represents an alkylene group. The alkylene group contains only a restricted number of carbons so as to avoid excessively lowering the refractive index of the ester oil. Herein, it is especially desirable to select alkylene groups containing from 2 to 4 carbons. Herein, it is particularly preferred to employ an alkylkene group having a pendant alkyl group such as methyl or ethyl so as to improve other physical properties of the ester oil, such as appearance or sensory properties. Especially desirably, the alkylkene group is isopropylene viz —CH(Me)—$CH_2$—.

When Y represents a bond, the alkylene group is bonded directly to aryl group $R^2$. Preferably Y represents an ester or ether linkage. In a number of highly desired embodiments X and Y together represent —CH(Me)—$CH_2$—O— or —CH(Me)—$CH_2$—$O_2$C— and especially —CH(Me)—$CH_2$—O—.

The ester oil of formula 1 herein (the invention oil) can constitute if desired the entire oil phase. However, if desired and where the formulator considers it to be appropriate, the oil phase can comprise one or more additional oil components, by which is meant components which are miscible with the invention oil. Such additional oil components can be chosen from oils, sometimes alternatively referred to as water-immiscible oils, that have hitherto been proposed for use in or employed as a carrier oil component in antiperspirant compositions.

Preparation of the Ester Oils

The ester oils according to formula 1 herein can be made by one or more literature esterification routes for making benzoic acid esters, by reacting the corresponding alcohol with benzoic acid, for example in an acid catalysed reaction, p-toluene sulphonic acid, at elevated temperature usually above 100° C., or likewise in a transesterification reaction. Reactants are often employed in an approximately stoichiometric mole ratio (1:1 for a monohydric alcohol: carboxylic acid, 1:2 for a dihydric alcohol:carboxylic acid). To assist the reaction, it can be conducted under a vacuum, for example below 400 mbar. The reaction is conveniently continued until the acid number has fallen below a preset value, indicating consumption of a substantial fraction of the carboxylic acid.

Additional Carrier Oils

The water-immiscible carrier liquid for the continuous phase comprises one or a mixture of materials which are relatively hydrophobic so as to be immiscible in water. Following partition between the continuous phase and the disperse phase, a small fraction of hydrophilic liquid may remain in the continuous phase, provided the overall carrier liquid mixture is immiscible with water. It will generally be desired that the carrier oils mixture is liquid (in the absence of gellant) at temperatures of 15° C. and above. It may have some volatility but its vapour pressure will generally be less than 4 kPa (30 mmHg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

In some embodiments, the carrier oil blend includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It can be desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m²/sec (10 centistokes), and particularly above $10^{-7}$ m²/sec (0.1 centistokes), the linear siloxanes normally exhibiting a viscosity of below $5 \times 10^{-6}$ m²/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The silicone oils employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include products available under the trademarks Dow Corning 556 and Dow Corning 200 series. Other non volatile silicone oils include that bearing the trademark DC704. The non volatile silicone oil can also comprise an aryl substituted siloxane which satisfies the general formula

as described in WO2004/071476 pages 7 to 12, and especially diphenylethyl substituted siloxanes which have a refractive index of above 1.5.

Incorporation of at least some non-volatile silicone oil having a high refractive index such as of above 1.5, e.g. at least 10% by weight (preferably at least 25% to 100% and particularly from 40 to 80%) of the silicone oils is often beneficial in some compositions, because this renders it easier to match the refractive index of the constituents of the composition and thereby easier to produce transparent or translucent formulations.

The proportion of silicone oils is at the discretion of the formulator and in many embodiments is from 0% to 80% by weight of the oils blend. Preferably, there is sufficient liquid silicone to provide at least 10% by weight of the oils blend, and especially employing liquid silicones having a refractive index of above 1.5.

Alternative oils include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms. Such oils can be contemplated to provide from 0 to 50% of the oils blend and in many instances from 0 to 20% thereof.

Other suitable additional oils comprise liquid aliphatic or aromatic esters. Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable additional liquid aromatic esters, preferably having a melting point of below 20° C., include fatty alkyl benzoates. Examples of such esters include suitable $C_8$ to $C_{18}$ alkyl benzoates or mixtures thereof, including in particular $C_{12}$ to $C_{15}$ alkyl benzoates e.g. those available under the trademark Finsolv. An aryl benzoate, such as benzyl benzoate can also be used, though preferably in an amount that does not significantly impair sensory properties, such as not more than 5%, preferably less than 3% and especially less than 1% of the weight of the oils blend.

Other suitable oils comprise liquid aliphatic ethers derived from at least one fatty alcohol, such as myristyl ether derivatives e.g. PPG-3 myristyl ether or lower alkyl ethers of polygylcols such as an ether having named as PPG-14 butyl ether by the CTFA.

In certain embodiments it is highly desirable to include one or more aliphatic alcohols which are liquid at 20° C., preferably having a melting point of not higher than 30° C. and it is especially desirable to employ those which are water-immiscible, and particular those having a boiling point of higher than 100° C. These include branched chain alcohols of at least 10 carbon atoms and in many instances up to 30 carbon atoms, particularly 12 to 26, such as isostearyl alcohol, hexyl-decanol, octyl-dodecanol and 2-decyl-tetradecanol. Other suitable water-immiscible alcohols include intermediate chain length linear alcohols, commonly containing from 9 to 13 carbon atoms, such as decanol or dodecanol. A further suitable alcohol is benzyl alcohol. A suitable proportion of such alcohols, and especially such water-immiscible alcohols of the liquid carrier is from 10 to 45% w/w.

It will be recognised that in some advantageous embodiments, the proportions of the oil constituents are selected so as to achieve refractive index (sometimes abbreviated herein to RI) matching with the suspended particulate or dissolved antiperspirant active. This tempers and qualifies the disclosures made previously herein with respect to proportions of oil constituents that are employable. In practice a mixture of oils will normally be employed, unless a single oil has an RI which matches that of the suspended active. The choice of oils will often be made in conjunction with the choice of suspended active. The choice of oils can be made within the same class of oils where those oils can combine to generate a suitable RI (obtained by a weight average of the RIs of constituent oils) or by combination of oils from two or more classes of oils. Thus, by way of example, an alkyl benzoate oil having an RI of about 1.484 can be combined in a suitable proportion with an invention oil with an RI in the region of 1.53 to 1.56 to attain a matching RI to that of an aluminium chlorohydrate antiperspirant salt having for example about 1.51 to 1.53. Likewise, a fraction of the oils blend can comprise a branched aliphatic alcohol or benzyl alcohol, for example replacing some or all of the alkyl benzoate oil.

In addition to the invention oil, a fraction of the oils blend can be provided by a non-volatile silicone oil and especially by one having a refractive index of above 1.5. Such non-volatile high RI silicone oils include by way of example linear siloxanes which are substituted by a significant fraction of aryl, (especially phenyl) groups instead of methyl groups, having a ratio of from 0.7 to 1.2 phenyl groups per Silicon atom. One commercially available example comprises DC704™ which is available from Dow Corning Inc. Linear di or tri-siloxanes with a similar density of phenyl groups are likewise employable. The proportions of the various oils that can be employed and still achieve RI matching depends naturally on not only their own RI but also on the RI of the active that is suspended in the blend. Thus, the invention oils and blends containing them are useful for suspending any aluminium or aluminium/zirconium antiperspirant active, be they in particulate form or dissolved in a polar liquid such as water to form an emulsion.

The Refractive Index employed herein for an oil is that listed or measured at 23° C., unless otherwise expressly indicated. Data-sheets for commercially available cosmetic oils commonly include the refractive index, and where not included, it can be measured conveniently using commercially available refractometers, such as an RFM 340™ Refractometer available from Bellingham and Stanley Ltd. Refractive index matching is made herein at or for 23° C. unless otherwise expressly stated.

Although the instant invention oils are especially suitable for anhydrous compositions in which a particulate antiperspirant active is suspended in the oil or an oil blend, the invention also encompasses compositions in which the antiperspirant active is dissolved in a polar liquid such as water or an aqueous blend. In such emulsions, the resultant suspended phase is commonly significantly lower than for the particulate antiperspirant. This means that RI matching can be achieved employing a very high proportion of materials with a low RI such as volatile silicone oils only a relatively low proportion of invention oil.

Accordingly, it will be seen that the high RI of the invention oils provides greater flexibility to the formulator in improving combinations of physical attributes of the compositions simultaneously.

Polar Liquids

Certain embodiments of the present invention comprise emulsions contain a solution of the antiperspirant active in a more polar or lypophobic disperse phase. The disperse phase in emulsions herein commonly comprises water as a solvent and can comprise one or more water soluble or water miscible liquids in addition to or in replacement of water. The proportion of water in such emulsions according to the present invention is often selected in the range of up to 60%, and particularly from 10% up to 40% or 50% of the whole formulation.

One class of water soluble or water-miscible liquids comprises short chain monohydric alcohols, e.g. $C_1$ to $C_4$ and especially ethanol or isopropanol, which can impart a deodorising capability to the formulation. Ethanol gives a cooling effect on application to skin, because it is very volatile. It is preferred that the content of ethanol or any other monohydric alcohol with a vapour pressure above 1.3 kPa (10 mmHg) is not over 15%, better not over 8% by weight of the composition.

A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycols, such as, particularly, 1,2-hexane diol, diethylene glycol, dipropylene glycol, 2-ethoxyethanol, diethylene glycol monomethylether, triethyleneglycol monomethylether and sorbitol. Especially preferred are propylene glycol and glycerol.

In emulsions herein the disperse phase normally constitutes from 5 to 80 or 85% of the weight of the composition preferably from 5 to 50 or 65% and more preferably from 25 or 35% up to 50, or 65%, while the emulsifier and the continuous phase with the structurant system and any water-immiscible cosmetic actives therein provides the balance. The weight proportion of continuous phase including the structurant normally constitutes from 15 or 35% up to 95% of the weight of the composition. Compositions with high proportion of disperse phase, i.e. from 65 to 85% disperse phase, may be advantageous because they can give good hardness even though the concentration of structurant may be only a small percentage of the total composition. However, compositions with a lower proportion of disperse phase can also be advantageous because they tend to offer a drier and warmer feel.

Compositions herein in the form of emulsion will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10 to 25, steareth-10 to 25 (i.e. $C_{16}$ and/or $C_{18}$ alcohols ethoxylated with 10 to 25 ethylene oxide (EO) residues) and PEG-15 to 25 stearate or distearate. Other suitable examples include $C_{10}$-$C_{20}$ fatty acid mono, or diglycerides. Further examples include $C_{18}$-$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlacel™, Brij™, Cremophor™, Dehydrol™, Dehymuls™, Emerest™, Lameform™, Pluronic™, Prisorine™, Quest PGPH™, Span™, Tween™, SF1228™, DC3225C™ and Q2-5200™.

Antiperspirant Actives

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Such activated aluminium chlorohydrates are made by a method in which the weight concentration of aluminium compounds in the solution is controlled within specified limits and simultaneously the temperature of that solution is controlled within a specified elevated temperature range whilst polymeric aluminium species are formed, and drying conditions are strictly controlled as described in the said EP-A-6739. Some activated salts do not retain their enhanced activity in the presence of water but are useful in substantially anhydrous formulations, i.e. formulations that do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have co-ordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis, though with differing particle size distributions. Consequently, such actives would become suitable for employment in the instant invention if their production has been suitably adapted to meet the invention particle size criteria.

Translucent or Transparent Compositions

Herein, in compositions intended to be translucent or transparent, the RIs of the antiperspirant active (be it in the form of particles or droplets) and the carrier oil (blend) are advantageously matched to within 0.02. Herein, RIs and differences between them are those at 22° C. unless otherwise specified. Preferably, the difference between the refractive indices is less than 0.01 and especially less than 0.005. This can be achieved by varying the proportions of liquids constituting the carrier, its resultant RI being a weight averaged RIs of the carrier constituents and/or by varying the RI of the antiperspirant active as indicated above. Under many circumstances, RI matching of the constituents of the invention formulations is not absolutely perfect, but is sufficiently close to achieve acceptable clarity. The RI of particulate antiperspirant active can also be modified by surface known treatments and the RI of antiperspirant solution by varying the concentration of the active and the incorporation of glycols, glycerol, and dissolving other mineral salts.

Small variations can arise in practice, for example from changes in temperature or between different batches of ingredients. Thus, such RI difference in the invention compositions herein on the shelf or in the home is often at least 0.0005, and sometimes at least 0.001. Advantageously, by selecting the particulate antiperspirant active in accordance with the criteria described herein, and particularly with increasingly preferred criteria, the benefit of clear formulations can be retained even when the above-mentioned RIs do not match exactly.

The proportion of solid antiperspirant salt in a suspension composition normally includes the weight of any water of hydration and any complexing agent that may also be present in the solid active. The particulate antiperspirant employed in the instant invention has a refractive index (RI) of at least 1.49 and not higher than 1.57. Actives which are free from zirconium tend to have an RI of from 1.49 to 1.54, depending on their formula and at least partly on their residual water content. Likewise, actives which contain zirconium tend to have an RI of from 1.52 to 1.57. The water content of the antiperspirant active can be modified by hydration after dried active has been made or by drying to an intermediate water content. The actives can also be treated with a small amount of an alcohol such a $C_2$ to $C_4$ aliphatic alcohol, eg ethanol, to alter its RI.

The RI of particulate material, viz the antiperspirant salt can be measured by a conventional Becke line method in which particles of the solid are suspended in a range of oil drops, each of different, but known RI, and the suspension is viewed through a microscope. The particle has a coloured fringe that moves into the oil phase or towards its centre as the focus of the instrument is slightly altered, the direction depending on which has the higher RI.

The particulate antiperspirant active when employed herein comprises small particles, of which desirably not more than 60% by weight, preferably not more than 50% and more preferably less than 40% by weight have a diameter of below 10 μm. Particularly preferably, between 40 and 25% of particles by weight have a particle size below 10 μm. In practice, desirable antiperspirant actives contain at least 1% and often at least 5% by weight of particles of at least 1 μM diameter in the range of from 1 to below 10 μM. In general, at least 90% by weight of the antiperspirant active has a particle size of below 100 μm, in many instances at least 95% by weight and in some preferred compositions at least 99% by weight below 100 μM. In many embodiments herein, the active has a weight average particle size of from 9 to 50 μm and particularly at least 10 μm, such as from 12 to 50 μm, and more preferably from 12 to 40 μm. It will be recognised, though that solid materials having such an average particle size are suitable only if they also meet the criterion given above about maximum proportion of particles below 10 μm being less than 60% by weight. An increase in product clarity is attainable by employing an active in which up to 25% by weight of the particles have a particle diameter of below 10 μm.

The fineness, coarseness and particle size distribution of antiperspirant actives that are produced can vary substantially, depending on their manner and conditions of manufacture, including the type of drying stage employed, and any subsequent processing stages, such as milling, and/or classification. Actives having an appropriate particle size distribution to satisfy the above selection criterion can be made by suitably controlling conventional drying and milling techniques in manners known to persons skilled in the art of making antiperspirant actives, so as to reduce the proportion of particles produced of sub 10 μm diameter. Methods can include control of droplet size in spray drying. Where a product is produced, for example by spray drying or freeze drying that has excessive proportion of sub 10 μm diameter particles, the proportion can be lowered by conventional classification apparatus.

Furthermore, it is highly desirable to employ particulate antiperspirant active material which is free or substantially free from hollow particles. In this context, substantially free indicates a content of less than 10% by weight hollow spheres, and preferably less than 5% by weight. Some drying techniques, eg spray drying, can produce materials which contain greater than such a proportion of hollow spheres. The proportion of hollow spheres in an antiperspirant material can be reduced until they are absent or substantially absent by milling the particulate material, such as by ball or swing milling. Products with no more than a few hollow particles (i.e. substantially absent) are considered to have no significant effect on the RI of the product—i.e. any effect is de minimis.

The proportion of antiperspirant active to employ is at the discretion of the formulator. Normally the proportion is in the range of from 1% up to 40%. Where the antiperspirant active is intended to provide deodorancy, the proportion is often chosen in the range of from 1 to 5% by weight and for suppression of sweating as well as deodorancy, the proportion is greater than 5% and usually from 10 to 30% by weight of the composition. The proportion of antiperspirant in many favoured compositions is from 15 to 26% by weight.

Thickeners and Structurants (Gellants)

Herein the compositions can be in the form of a liquid or a gel, depending on whether a gellant is incorporated. In liquid formulation, the oil blend can be thickened by one or more oil thickeners. These thickeners can include, if desired, polymeric thickeners such as cellulose and starch polymeric derivatives that are oil soluble, such a dextrin esters, eg dextrin palmitate or other oil-soluble polymers. Such polymers can include polyethylene having a mol weight of 2000 to 8000, polystyrene or poly α methylstyrene eg Kristalex F85™, block copolymers of styrene with ethylene, propylene and/or butalene, eg Kraton™ copolymers, copolymers of polyvinylpyrrolidone with polyethylene, eg Antaron WP-660™ copolymer and polyamide thickeners according to USPP550209 such as Versamid 950 polyamide. The proportion of thickener is often employed in the range of from 0.1 to 15% by weight and in many instances is for 0.2 to 5% by weight, depending on the extent of thickening (and hence vicosity increase) that is desired.

Alternatively, the invention compositions can be gelled to form either solids or soft solids (sometimes alternatively called anhydrous creams). The formulator is able to employ any gellant that has hitherto been contemplated or employed to gel an ester oil or oil blend containing an ester oil. Where the formulator is not concerned about whether or not he achieves a translucent or transparent formulation, he can employ any wax, according to U.S. Pat. No. 6,387,358. Such waxes include silicone waxes, hydrocarbon waxes including microcrystallines waxes, polyethylene waxes, Fischer-Trosch waxes, naturally-occurring waxes eg beeswax or spermacetti wax, or derivatives thereof such as siliconised beeswax, or waxy ester fractions of beeswax or synthetic ester waxes or waxes obtained by hydrogenating glyceride plant oils such as castor wax, carnauba wax or candellila wax. Waxy gellants include linear fatty alcohols of at least $C_{12}$ such as from $C_{12}$ to $C_{24}$, including cetyl stearyl and behenyl alcohols.

The invention compositions advantageously include as gellant a non-polymeric fibre-forming gellant, by which we mean materials that are either monomers or dimers having a molecular weight of below 10000 and which form a network of elongated strands when they solidify within a carrier oil or oil blend. These strands have an aspect ratio of greater than 10:1 and commonly on average of over 50:1. A particularly suitable class of fibre-forming gellants herein normally comprise one or more amide groups, the class including gellants having dipeptide linkages.

The employment of such fibre-forming gellants is especially beneficial in the context of producing translucent or transparent formulations, because the strands are sufficiently narrow for them not to be visible normally to the unassisted human eye, though they become apparent when subject to magnification. Accordingly, it is especially desirable to employ such gellants in conjunction with the antiperspirant active being RI matched with the carrier oil.

U.S. Pat. No. 5,750,096 is one of several documents which teaches that gelation can be brought about using amides of 12-hydroxy stearic acid with an alcohol containing an aliphatic, cycloaliphatic or aromatic group with up to 22 carbons therein. If the group is aliphatic it preferably contains at least three carbon atoms. If cycloaliphatic, it preferably contains at least five carbon atoms and may be a fixed ring system such as adamantyl.

Amide derivatives of other fatty acids with $C_8$ or longer alkyl chains may be used of which a specific example is lauric monoethanolamide also termed MEA lauramide.

N-acyl amino acid amides are particularly suitable gellants for hydrophobic liquids and are capable of forming transparent or translucent solid formulations. They are described in U.S. Pat. No. 3,969,087 to Ajinomoto. The acyl and amido substituents can be linear or branched. The amido groups often contain each from 2 to 10 carbons, including particularly butylamide groups. An advantageous selection from U.S. Pat. No. 3,969,087 has been disclosed in USA 2002/0159961 also to Ajinomoto in which the acyl substituent comprises 7 to 10 carbons, including especially branched substituents such as 2-ethyl-hexanoyl. N-Lauroyl-L-glutamic acid di-n-butylamide is commercially available from Ajinomoto under their designation GP-1. It is particularly desirable to employ a combination of GP-1 with its related gellant N-(2-ethylhexanoyl)-L-glutamic acid di-n-butylamide, since the combination improves the properties of anhydrous suspension formulations and stabilises emulsions.

Further materials which have been disclosed as gelling agents are the amide derivatives of di and tribasic carboxylic acids set forth in WO 98/27954 notably alkyl N,N'dialkyl succinamides.

A further class of fibre-forming gellants comprises cyclo-dipeptides obeying the formula

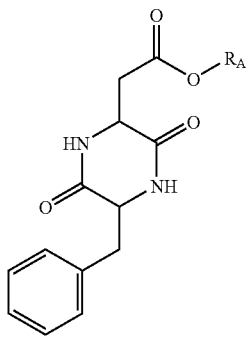

in which $R_A$ represents an aliphatic or preferably a carbocyclic or heterocyclic group containing not more than 2 rings and X represents O or NH. These gellants are described in WO 03/059307. $R_A$ can comprise two fused rings, but preferably comprises a single six membered ring, either carbocyclic or heterocyclic, or a bridged ring. When $R_A$ is carbocyclic, it can be either saturated or unsaturated, preferably unsaturated or aromatic. When $R_A$ is heterocyclic, it is preferably saturated. Preferred examples include $R_A$ residues include menthol, isopinocamphenol and 3,5-dialkyl cyclohexanol such as 3,5-dimethyl cyclohexanol. Especially preferred $R_A$ residues include thymol. Cyclodipeptide gellants are especially suitable gellants for making transparent or translucent solid formulations.

A further class of fibre-forming gellants comprises 1,2-di-amido-substituted cyclohexane, and particularly such compounds in which each amido substituent accords with the general formula —$(CH_2)_v$—NH—CO—$R^{111}$) in which $R^{111}$ represents an alkyl group of from 5 to 27 carbon atoms and v is an integer selected from zero and one, and preferably v is zero. $R^{111}$ can be linear or branched. Preferably the number of carbons in $R^{111}$ is selected in the range of 8 to 20. For example undecyl, dodecyl, 2-ethylhexyl, octadecyl, or dimethyloctyl.

The invention compositions can employ a combination of a sterol and a sterol ester gellant system as described in U.S. Pat. No. 6,231,841. A preferred system within the range of sterols and sterol esters or campesterol or cholesterol, or a hydrogenated derivative thereof, such as dihydrocholesterol, or especially β-sitosterol in conjunction oryzanol, and particularly γ oryzanol. The mole ratio range is desirable from 3:1 to 1:2.

Further gellants which can be contemplated for use in the present invention compositions herein include oil-soluble copolymers of polyamide or polyurethane or polyurea or polyurethane/urea with polysiloxane. Suitable copolymers are the copolymers described in U.S. Pat. No. 5,919,441 from col 18 line 31 through to col 27 line 31. Desirable silicone based polyamides are described in U.S. Pat. No. 6,051,216 col 6 line 6 through to col 9 line 52. Siliconised polyamides suitable for the preparation of clear products are as described in U.S. Pat. No. 6,451,295 in col 6 line 37 through to col 17 line 50.

The gellants are often employed in a proportion of from 0.5 to 35% by weight of the composition, the actual proportion being selected in accordance with the effectiveness of the gellant at gelling, the hardness or softness of the desired gelled product and also the manufacturing technique. In many embodiments, the waxes when employed are selected in a range of from 1 to 8% by weight when softer products are desired and from 10 to 25% often 13 to 20% when harder compositions are desired. Fibre-forming gellants are preferably employed in a proportion of from 1 to 20% and particularly from 1 up to 15%, desirably to the extent of their solubility at 100° C. Amide-substituted cyclohexanes are most preferably employed at a concentration of from 7.5 to 15% by weight, whereas N-acyl amino acid diamides and cyclodipeptides are preferably employed at a concentration selected in the range of from 1 to 10% by weight of the composition.

Optional Ingredient

Optional deodorant actives include deoperfumes, and/or microbicides, including particularly bactericides, such as chlorinated aromatics, including biguanide derivatives, of which materials known as Irgasan DP300™ (triclosan), Tricloban™, and chlorhexidine warrant specific mention. A yet another class comprises biguanide salts such as are available under the trade mark Cosmosil™. Deodorant actives are commonly employed at a concentration of from 0.1 to 25% by weight.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts conventionally contemplatable for cosmetic solids or soft solids. A moisturiser such as glycerol, for example in an amount of up to about 5%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

The composition can conveniently adopt any form known for an antiperspirant composition and be incorporated in its respective dispenser, that is to say a liquid suitable for being dispensed from a roll-on or alternate liquid contact applicator, or by conversion into a spray via a squeeze spray or pump-spray applicator known in themselves. The liquid composition may alternatively be incorporated onto an absorbent pad or sheet. The liquid composition may be thickened to the viscosity desired by the formulator for optimised dispensing from the selected applicator. The liquid composition may be gelled to form a soft solid or solid employing the gellants described hereinbefore.

Alternatively, the compositions can be in the form of aerosol compositions employing a propellant such as a hydrocarbon having a boiling point of below 5° C. and especially below −5° C. Examples of such propellants include propane, isopropane butane and isobutane. Other hydrocarbons worthy of consideration include pentane or isopentane. Other propellants that are worthy of incorporation include fluorohydrocarbons that likewise have the boiling points indicated above. It will be recognised that herein, in the context of aerosol compositions that contain additionally a propellant, concentrations of ingredients other than the propellant relate to the base composition, that is to say the composition containing all ingredients except the propellant. In aerosol compositions, the propellant is often present in a weight ratio of from 14:1 to 2:3, and in many embodiments from 8:1 to 3:2. The base composition is especially desirably a liquid, optionally thickened, to ease its discharge through the spray outlet of an aerosol dispenser.

Composition Preparation

The compositions herein can be made by processes hitherto described for the preparation of cosmetic compositions in liquid form or for the formation of thickened or gelled compositions containing ester oils, such as $C_{12-15}$ alkyl benzoates.

Having described the invention in general terms specific embodiments thereof will be described hereinafter in greater detail and by way of example only.

| | Ingredients | | |
|---|---|---|---|
| 1 | DG-1 | 2-propanol, 1-phenoxy benzoate | |
| 2 | DC245 ™ | Cyclomethicone | Dow Corning |
| 3 | Prisorine 3515 ™ | Isostearyl alcohol | Uniqema |
| 4 | Eutanol G16 ™ | hexyl decanol | Cognis |
| 5 | DC704 ™ | 1,1,5,5-tetraphenyl trisiloxane | Dow Corning |
| 6 | Finsolv TN ™ | C12-15 Alkyl Benzoate | Finetex |
| 7 | DG-2 | propylene glycol dibenzoate | |
| 8 | A418 ™ | Milled Macrospherical AACH ~20% of particles <10: m. Material contains few hollow particles. RI 1.530 | Summit |
| 9 | AP5G-LR ™ | Al/Zr pentachlorohydrex glycine complex (sample) [RI 1.528, 20% <10: m, few hollow particles | B K Giulini GmbH |
| 10 | Reach 908 ™ | Al/Zr tetrachlorohydrex glycine complex | Reheis Inc |

-continued

| | Ingredients | | |
|---|---|---|---|
| 11 | GP-1 ™ | N-lauroyl-L-glutamic acid Di-n-butylamide | Ajinomoto |
| 12 | GA-01 ™ | N-2-ethyl hexanoyl)-L-glutamic acid Di-n-butylamide | Ajinomoto |
| 13 | | Stearyl alcohol | Cognis |
| 14 | Castorwax MP80 ™, | hydrogenated castor oil | CasChem |
| 15 | Talc IMP 1888L ™ | talcum powder | Paroxite Ltd |
| 16 | Tenox BHT ™: | Butyl hydroxy toluene | Eastman Chemicals |
| 17 | | PEG 8-Distearate | Stepan |
| 18 | Aloxicoll L ™ | ACH solution (50% w/w) | B K Giulini GmbH |
| 19 | Bentone 38 ™ | Quaterium-18 hectorite | Rheox |
| 20 | Abil EM90 ™ | cetyl dimethicone copolyol | Goldschmidt |
| 21 | water | demineralised water | in-house |
| 22 | CAP 40 ™ | propane, butane, isobutane | Calor |

Ingredient DG1 was prepared by mixing phenoxy-2-propanol (379.9 g) with benzoic acid (320.1 g) in the presence of p-toluenesulphonic acid (4.2 g) and phosphinic acid (0.7 g) heating the mixture to 160° C. and applying a vacuum to 400 mbar. After 1.5 hours, the vacuum was increased to 200 mbar and subsequently to 309 mbar. The temperature was then raised to 180° C. and the acid number of the mixture measured periodically. When the acid number reached <15, the mixture was neutralised with potassium hydroxide solution and steam treated. The ester oil was then dried at 150° C. under vacuum, cooled and filtered to produce a clear, pale yellow liquid with 90% purity (by GC) in a yield of 95% based on the alcohol. The ester oil DG-1 had an RI of 1.5478 and a viscosity at 25° C. of 60 mPas (with a Brookfield viscometer). It has the structure:

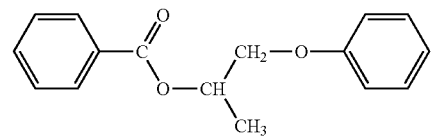

Ingredient DG2 was prepared by a corresponding process to that for DG-1, but employing 1,2-propylene glycol in a mole ratio to benzoic acid of about 1:2. The ester oil DG-2 at 25° C. had a refractive index of 1.5423 and a viscosity of 90 mPas. It has the structure:

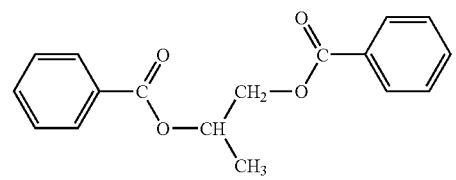

EXAMPLES

Example 1

Clear Suspension Sticks

In a preliminary step, the refractive indexes of the oils and the antiperspirant active employed in the Example and comparison products were measured at 23° C. or identified from product literature and if necessary converted to 23° C., the proportions of the oils being calculated so as to closely match the RI of the antiperspirant active.

The sticks in Examples 1.1 to 1.4 and comparisons 1.A and 1.B were made by the following method:—

All of the carrier oils, (4, 5 and if employed 1) and the structurants (11 and 12) were weighed into a glass vessel, mixed using a Heidolph™ mixer with 4 blade paddle stirrer at 150 rpm and heated to over 100° C. using a hotplate until all of the structurant had visibly dissolved. The heat was then removed and the temperature was allowed to fall to 90-95° C. The fragrance was then added. During that time the antiperspirant salt (8 or 9) was weighed into container with air tight lid heated in an oven to 45° C. The particulate antiperspirant salt was then slowly added to the solution of the structurants in the carrier oils whilst increasing the paddle rate to 200 rpm to ensure thorough dispersion of the particulates. The resultant mixture was then was allowed to cool slowly and its solidification temperature assessed. In a subsequent run, the composition was allowed to cool at the same rate until it had reached about 5° C. above the solidification temperature, whereupon then poured into conventional antiperspirant stick barrels and allowed to fully cool. Characterisation (Hardness and Clarity) was carried out after the formulation had been left to stand at room temperature for at least 48 hours.

The compositions and properties are summarised in Table 1 below.

TABLE 1

|  | Comp 1.A | Ex 1.1 | Ex 1.2 | Comp 1.B | Ex 1.3 | Ex 1.4 |
|---|---|---|---|---|---|---|
| DC704 (5) | 57.01 | 43.504 | 29.52 | 56.18 | 42.61 | 28.92 |
| Eutanol G-16 (4) | 11.99 | 10.994 | 9.96 | 13.82 | 12.19 | 11.17 |
| DG-1 (1) |  | 14.501 | 29.52 |  | 14.2 | 28.92 |
| A418 (8) | 25 | 25 | 25 |  |  |  |
| Zirkonal AP5G-LR (9) |  |  |  | 25 | 25 | 25 |
| GA-01 (12) | 2.5 | 2.5 | 2.5 | 2.5 | 2.5 | 2.5 |
| GP-1 (11) | 2.5 | 2.5 | 2.5 | 2.5 | 2.5 | 2.5 |
| Fragrance | 1 | 1 | 1 |  | 1 | 1 |
| Properties |  |  |  |  |  |  |
| Hardness (mm) | 9.46 | 8.2 | 7.78 | 9.86 | 9.09 | 7.81 |
| Clarity % T | 15.69 | 9.41 | 12.81 | 3.94 | 5.1 | 4.95 |
| Pour Temp (° C.) | 90 | 80 | 80 | 78 | 74 | 72 |
| Gel Temp (° C.) | Tg ~85 |  |  |  |  |  |

From a comparison of Comp 1.A with Examples 1.1 and 1.2, and of Comp 1.B with Examples 1.3 and 1.4, it can be seen that the sticks according to the Examples 1.1 and 1.2 were harder than the corresponding comparison stick Comp 1.A, and advantageously, the invention compositions could be poured at a lower temperature, thereby rendering the manufacturing process significantly easier. Further more, the Example compositions had a less wet and oily feel when applied onto the skin than did the comparison Comp 1.A, the benefit from Ex1.2 being greater than for Ex1.1. The same advantages accrued to Examples 1.3 and 1.4 in comparison with Comp 1.B.

Examples 1.5 to 1.9 and Comparison 1.C

The sticks in Examples 1.5 to 1.8 and Comparison 1.C were made in a similar manner to the previous Examples and Comparisons, except that structurants were dissolved in the fatty alcohol which mixture was thereafter cooled to 95° C. whereas the remaining carrier oils were mixed with the antiperspirant active and heated to 90° C. before being slowly added into the structurant solution in a high shear Silverson™ mixer and finally fragrance was added. The mixture was likewise poured at a temperature of 5° C. above the predetermined solidification temperature and the properties of the stick measured when the stick had stood at ambient temperature for at least 48 hours.

The compositions of Comparisons 1.A and 1.C and Examples 1.5 to 1.9 and their properties are summarised in Table 2 below.

TABLE 2

|  | Ex 1.5 | Ex 1.6 | Ex 1.7 | Comp 1.C | Comp 1.A | Ex 1.8 | Ex 1.9 |
|---|---|---|---|---|---|---|---|
| ISA (3) | 10.35 | 10.43 | 10.5 | 13.11 |  |  |  |
| DC704 (5) |  |  |  | 55.89 | 57.01 | 43.98 | 30.19 |
| Eutanol G-16 (4) |  |  |  |  | 11.99 | 10.36 | 8.62 |
| DG-1 (1) | 58.65 | 59.07 | 59.5 |  |  |  |  |
| DG-2 (7) |  |  |  |  |  | 14.66 | 30.19 |
| A418 (8) | 25 | 25 | 25 | 25 | 25 | 25 | 25 |
| GA-01 (12) | 2.5 | 2.25 | 2 | 2.5 | 2.5 | 2.5 | 2.5 |
| GP-1 (11) | 2.5 | 2.25 | 2 | 2.5 | 2.5 | 2.5 | 2.5 |
| Fragrance | 1 | 1 | 1 | 1 | 1 | 1 | 1 |
| Properties |  |  |  |  |  |  |  |
| Hardness (mm) | 8.8 | 9.2 | 10 | 9.5 | 9.46 | 9.10 | 8.71 |
| Clarity % T | 13.78 | 8 | 7.3 | 17.46 | 15.69 | 8.55 | 17.12 |
| Pour Temp (° C.) | 85 | 83 | 80 | 90 | 90 | 79 | 80 |
| Gel Temp (° C.) |  |  |  | Tg ~85 | Tg ~85 | Tg ~74 | Tg ~74 |

From a comparison of Example 1.5 to 1.7 with Comp 1.C, it an be observed that at the same concentration of structurants (5%) the invention composition was harder and even so enjoyed a lower pour temperature. This enabled the concentration of the structurants to be reduced by about 14% to achieve the same hardness, and this in turn further lowered the pour temperature. The Examples once again was less oily and less wet in feel than was comparison 1.C. Likewise, the example compositions 1.8 and 1.9 using invention oil DG2 had a lower pour temperature than the comparison Comp 1.A, and also were somewhat harder so that the reduction in pour temperature was not attributable to the compositions being softer. Likewise the Example compositions were less oily than the comparison Comp 1.A.

All the sticks in Example 1.1 to 1.9 and Comparisons 1.A to 1.C can be described as clear (comp B, Ex3 and 4 are translucent). Differences in light transmission can in part be attributed to the accuracy of RI matching of suspended particulate antiperspirant and carrier oils mix.

All the Example sticks 1.1 to 1.9 using ester oils DG1 or DG2 were free from the sensory negatives from use of a corresponding amount of benzyl benzoate, i.e. did not irritate the skin.

Example 2

Opaque Compositions

The sticks in Example 2.1 and Comparison 2.A were made by a conventional method for making a wax structured stick in which the linear fatty alcohol and hydrogenated glyceride oil (castor wax) structurants and the carrier oils were mixed together and heated to about 85° C. to form a single phase, which continued to be stirred. It was allowed to cool around 75° C. and then the particulate antiperspirant active was introduced followed by the talcum powder, BHT and fragrance in that order. The final mixture was poured into the conventional barrels at a temperature of about 5° C. about the predetermined solidification temperature and the properties of the sticks determined after the cooled sticks had been stored at ambient temperature for at least 48 hours. The compositions and results are summarised in Table 3 below.

TABLE 3

|  | Comp 2.A | Ex 2.1 |
| --- | --- | --- |
| Finsolv TN (6) | 17.5 |  |
| DC245 ((2) | 33.7 | 33.7 |
| DG-1 (1) |  | 17.5 |
| Reach 908 (10) | 24 | 24 |
| Stearyl Alcohol (13) | 17.5 | 17.5 |
| Castorwax MP-80 (14) | 2.5 | 2.5 |
| PEG-8 Distearate (17) | 2 | 2 |
| Talc (15) | 2 | 2 |
| BHT (16) | 0.05 | 0.05 |
| Fragrance | 0.75 | 0.75 |
| Properties |  |  |
| Hardness (mm) | 6.2 | 6 |
| Pour Temperature (° C.) | 58 | 54 |

From Table 3, it can be seen that the Example composition had a lower pour temperature than the comparison composition Comp 2.A even though the product was harder. The film deposited on the skin from the invention composition was also dryer and less oily than that from the comparison composition.

The Example composition Ex 2.1 was free from the sensory negatives from use of a corresponding amount of benzyl benzoate, i.e. did not irritate the skin.

Example 3

Liquid and Aerosol Formulations

Liquid formulations having the compositions summarised in Table 4 below are prepared by mixing the constituents together at ambient temperature. Aerosol compositions are thereafter made by charging aerosol containers with the liquid compositions, and thereafter pressurising by introduction of the propellant.

TABLE 4

|  | Ex 3.1 | Ex 3.2 |
| --- | --- | --- |
| Liquid composition | % w/w of liquid composition | |
| DC245 (2) | 30.0 | 23.7 |
| DG-1 (1) | 23.1 | 8.0 |
| AACH (8) | 38.5 |  |
| Aloxil L (18) |  | 40.0 |
| Bentone 38 (19) | 3.8 |  |
| Abil EM90 (20) |  | 0.4 |
| water (21) |  | 26.7 |
| fragrance | 4.6 | 1.2 |
| Aerosol composition | % w/w of aerosol composition | |
| Liquid composition | 13 | 50 |
| propellant (22) | 87 | 50 |

Measurement of Properties

Refractive Index

The refractive index of respective materials were measured at room temperature (23° C.) unless otherwise stated, employing a Becke line test (a standard procedure) for the antiperspirant active and an RFM340™ refractometer from Bellingham and Stanley Ltd for the ester oils. Each oil was diluted with a known diluent, isostearyl alcohol [RI=1.456] in predetermined weight ratios, the refractive index of each mixture being measured and plotted against the weight proportion of the ester oil. The refractive index of 100% ester oil was then determined by extrapolation.

Viscosity

The viscosities if the ester oils were measured at 25° C. in a conventional manner using a Brookfield viscometer.

Quiescent Gelling Temperature ($T_g$)

The quiescent gelling temperature ($T_g$) of the carrier/mixture was determined by preparing a solution of the structurant in the carrier/mixture in a glass vessel equipped with a glass thermometer resting on the bottom of the vessel, in accordance with the Examples herein, and thereafter permitting the resultant solution to cool naturally under quiescent conditions, ie without any cooling air being blown over the vessel and without the solution being stirred. External laboratory air temperature was about 23° C. Periodically, the thermometer was lifted by a few mm and if liquid had not flowed to fill the void under gravity, was carefully replaced on the vessel bottom. The solution was considered to have formed a gel when it did not flow back underneath the thermometer.

Hardness

The hardness and rigidity of the sticks were measured by penetrometry. The procedure utilises a lab plant PNT penetrometer equipped with a Seta wax needle (weight 2.5 grams) which has a cone angle at the point of the needle specified to be 9°10'+/−15". A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

Clarity

The clarity of a composition (% T) was measured by placing a sample of standardised thickness in the light path of a spectrophotometer and measuring transmittance, as a percentage of light transmitted in the absence of the gel.

This test was carried out using a dual-beam Perkin Elmer Lambda 40 spectrophotometer. The sample of composition was poured hot into a 4.5 ml cuvette made of poly(methylmethacrylate) (PMMA) and allowed to cool to an ambient temperature of 20-25° C. Such a cuvette gives a 1 cm thickness of composition. Measurement was carried out at 580 nm, with an identical but empty cuvette in the reference beam of the spectrophotometer, after the sample in the cuvette had been held for 24 hours. A transmittance measured at any temperature in the range from 20-25° C. is usually adequately accurate, but measurement is made at 22° C. if more precision is required.

I claim:

1. An antiperspirant composition comprising an antiperspirant active and a carrier therefor in which the carrier comprises an aromatic ester oil satisfying the general formula:

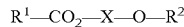

in which $R^1$ and $R^2$ each represent a phenyl group, X represents an alkylene group having at least one pendant alkyl group having 1 or 2 carbons, wherein X, inclusive of said at least one pendant alkyl group, has from 2 to 4 carbons, wherein the antiperspirant composition is in the form of a stick.

2. A composition according to claim 1 in which the aromatic ester oil has the formula Ph-$CO_2$—CH(Me)—$CH_2$—O-Ph.

3. A composition according to claim 1 in which the antiperspirant active is particulate and suspended in the carrier.

4. A composition according to claim 3 in which the antiperspirant active and the carrier have refractive indexes matched to within 0.02.

5. A composition according to claim 1 in which the carrier is thickened or gelled by the incorporation therein of a thickener or gellant.

6. A composition according to claim 5 in which the carrier is gelled by a polymeric gellant or by a non-polymeric fibre-forming gellant.

7. A composition according to claim 6 in which the non-polymeric gellant is selected from N-acyl aminoacid amides, cyclodipeptides, and diamido-substituted cyclohexane.

8. A composition according to claim 7 in which the gellant comprises N-lauroyl-L-glutamic acid di-n-butylamide and/or N-(2-ethylhexanoyl)-L-glutamic acid di-n-butylamide.

9. A composition according to claim 7 in which the carrier further comprises from 10 to 45% by weight thereof of water-immiscible monohydric alcohol having a melting point of not higher than 30° C. and a boiling point of higher than 100° C.

10. A composition according to claim 9 in which the monohydric alcohol is a branched chain aliphatic alcohol of from 12 to 26 carbons.

11. A composition according to claim 9 in which the antiperspirant active and the carrier have refractive indexes matched to 0.02.

12. A composition according to claim 9 in which the antiperspirant active and the carrier have refractive indexes matched to within 0.01.

13. A non-therapeutic method of ameliorating body odour or inhibiting perspiration in which a composition according to claim 1 is applied topically to skin.

* * * * *